(12) United States Patent
O'Connell et al.

(10) Patent No.: US 10,716,718 B2
(45) Date of Patent: Jul. 21, 2020

(54) ANTI-SKID MATERIAL FOR EARS OR FASTENING TABS OF ABSORBENT ARTICLE

(71) Applicant: First Quality Baby Products, LLC, Great Neck, NY (US)

(72) Inventors: Susan O'Connell, Chesterbrook, PA (US); Carol L. Erdman, West Chester, PA (US)

(73) Assignee: FIRST QUALITY BABY PRODUCTS, LLC, Great Neck, NY (US)

( * ) Notice: Subject to any disclaimer, the term of this patent is extended or adjusted under 35 U.S.C. 154(b) by 345 days.

(21) Appl. No.: 15/191,872

(22) Filed: Jun. 24, 2016

(65) Prior Publication Data

US 2016/0374872 A1 Dec. 29, 2016

Related U.S. Application Data

(60) Provisional application No. 62/185,305, filed on Jun. 26, 2015.

(51) Int. Cl.
*A61F 13/56* (2006.01)
*A61F 13/84* (2006.01)

(52) U.S. Cl.
CPC .......... *A61F 13/5622* (2013.01); *A61F 13/84* (2013.01)

(58) Field of Classification Search
CPC .............. A61F 13/5622; A61F 13/5633; A61F 13/5644; A61F 13/84
See application file for complete search history.

(56) References Cited

U.S. PATENT DOCUMENTS

| 5,151,092 A | 9/1992 | Buell et al. |
| 5,221,274 A | 6/1993 | Buell et al. |
| 5,242,436 A | 9/1993 | Weil et al. |
| 5,383,871 A | 1/1995 | Carlin et al. |
| 5,569,234 A | 10/1996 | Buell et al. |

(Continued)

FOREIGN PATENT DOCUMENTS

JP          63256702 A  * 10/1988

OTHER PUBLICATIONS

International Search Report for PCT/US2016/39219 dated Sep. 13, 2016.
Written Opinion for PCT/US2016/39219 dated Sep. 13, 2016.

*Primary Examiner* — Kathryn E Ditmer
(74) *Attorney, Agent, or Firm* — Amster, Rothstein & Ebenstein LLP

(57) ABSTRACT

An absorbent article that has a reduced tendency to shift when worn. The absorbent article includes a chassis with a front waist portion, a crotch portion, and a back waist portion. Side panels or ears are attached to the front and back waist portions of the chassis, and fastening components are attached to the back ears. Anti-skid elements are added to the outside surface and/or inside surface of the front side panels or ears and/or to the inside surface of the fastening tabs, such as by applying an elastomeric strip in a substantially vertical direction. When the absorbent article is fastened to the wearer attaching the fastening components on the back ears to the front waist portion of the absorbent article, the anti-skid elements interface with the front waist portion, the front ears, and/or the wearer to exert friction and thereby reduce shifting of the fastened absorbent article.

42 Claims, 10 Drawing Sheets

(56) References Cited

U.S. PATENT DOCUMENTS

| | | | |
|---|---|---|---|
| 5,782,819 A * | 7/1998 | Tanzer | A61F 13/15203 2/337 |
| 5,851,205 A * | 12/1998 | Hisada | A61F 13/5512 604/390 |
| 5,858,013 A | 1/1999 | Kling | |
| 6,030,373 A * | 2/2000 | VanGompel | A61F 13/58 24/442 |
| 6,258,076 B1 | 7/2001 | Glaug et al. | |
| 6,406,466 B1 * | 6/2002 | Pozniak | A61F 13/622 2/300 |
| 6,626,879 B1 * | 9/2003 | Ashton | A61F 13/496 604/385.01 |
| 6,911,407 B2 | 6/2005 | Sherrod et al. | |
| 6,918,900 B2 * | 7/2005 | Johnson | A61F 13/515 604/385.03 |
| 6,945,968 B2 | 9/2005 | Svensson et al. | |
| 7,074,215 B2 | 7/2006 | Ashton et al. | |
| 7,150,732 B2 * | 12/2006 | Yoshida | A61F 13/49011 604/389 |
| 7,569,042 B2 | 8/2009 | Van Gompel et al. | |
| 7,654,994 B2 | 2/2010 | Winkel et al. | |
| 7,754,939 B2 | 7/2010 | Yoshida et al. | |
| 8,152,787 B2 | 4/2012 | Faulks et al. | |
| 8,162,912 B2 | 4/2012 | Schlinz et al. | |
| 8,172,821 B2 | 5/2012 | Flannery | |
| 8,216,200 B2 | 7/2012 | Meetz et al. | |
| 8,262,636 B2 | 9/2012 | Sperl | |
| 8,518,006 B2 | 8/2013 | Faulks et al. | |
| 8,523,836 B2 | 9/2013 | Sperl | |
| 8,545,474 B2 | 10/2013 | Schilpp et al. | |
| 8,585,671 B2 | 11/2013 | Faulks et al. | |
| 8,636,710 B2 * | 1/2014 | Ellingson | A61F 13/5633 604/367 |
| 2002/0095130 A1 | 7/2002 | Seitter et al. | |
| 2004/0111076 A1 * | 6/2004 | Sayama | A61F 13/15203 604/385.13 |
| 2005/0283954 A1 | 12/2005 | Erdman et al. | |
| 2009/0299323 A1 | 12/2009 | Schlinz et al. | |

* cited by examiner

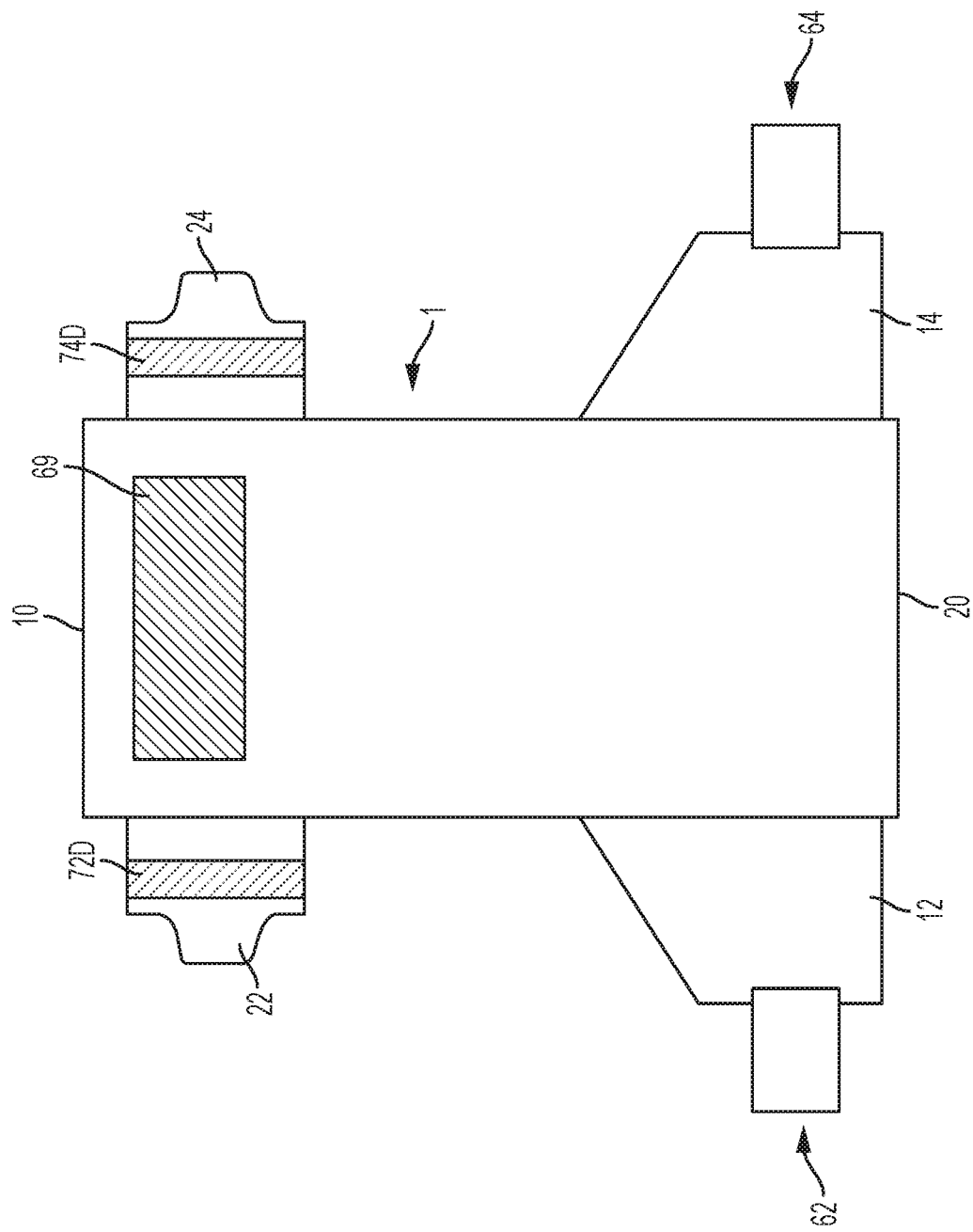

ANTI-SKID MATERIAL FOR EARS OR FASTENING TABS OF ABSORBENT ARTICLE

CROSS-REFERENCE TO RELATED APPLICATIONS

This application claims benefit of and priority to U.S. Provisional Patent Application No. 62/185,305, filed Jun. 26, 2015, the contents of which are incorporated by reference as if fully set forth herein.

FIELD OF THE INVENTION

The present invention relates generally to disposable absorbent articles such as disposable diapers, and more specifically to diapers having anti-skid material applied to the ears and/or fastening tabs to limit the shifting of the diapers when worn.

BACKGROUND OF THE INVENTION

Infants and other incontinent individuals wear disposable absorbent articles such as diapers to absorb and contain body exudates discharged from the body, particularly urine. Absorbent articles function to contain the discharged materials in isolation from the body of the wearer on one side, and from the wearer's garments and/or bedding on the other. Absorbent articles are well known in the art and are typically constructed from a combination of liquid and vapor pervious and impervious materials that respectively allow the passage of liquid into the diaper and prevent its exit therefrom.

A conventional disposable diaper has side panels, also referred to as ears, on a back waist portion. Fasteners (also referred to as fastening tabs) attached to the back ears of the disposable diaper are wrapped around toward the front waist of the wearer and fastened along the front waist portion of the diapers. This arrangement works well to prevent the passage of exudates. However, a conventional diaper sometimes shifts from an initial position after it is fastened on the wearer. The shifting of the diaper may be uncomfortable to the wearer and may result in sagging and leakage of some exudate.

SUMMARY OF THE INVENTION

An object of the present invention is to provide an absorbent article that does not shift while being worn. It is also an object of the present invention to reduce the shifting of the absorbent article while it is being worn.

According to an exemplary embodiment of the present invention, an absorbent article has an inside surface that faces a wearer's body when the absorbent article is worn, and an outside surface opposite the inside surface. The absorbent article comprises a chassis having a front waist portion with a first front ear on one side and a second front ear on the other side. The absorbent article also has a back waist portion comprising a first back ear on one side and a second back ear on the other side. A crotch portion of the absorbent article longitudinally extends between the front and back waist portions. The chassis includes a liquid pervious topsheet, a backsheet of which at least a portion is liquid impervious, and an absorbent core disposed between the topsheet and the backsheet. The absorbent article further comprises a first fastening component attached to the first back ear and a second fastening component attached to the second back ear for respective attachment to the front waist portion to fasten the absorbent article around the waist of the wearer.

In addition, the absorbent article comprises anti-skid elements. In embodiments, a first anti-skid element may be disposed along an outward-facing portion of the first front ear (i.e., facing toward an outer garment) and a second anti-skid element disposed along an outward-facing portion of the second front ear. Alternatively, or in addition, anti-skid elements may be added on the inward-facing portion of the first and second front ears.

Anti-skid elements may be included on the inside surfaces of the fastening tabs attached to the back ears to further prevent shifting and sagging when the article is worn. The anti-skid elements on the inside surfaces of the fastening tabs may be in addition to the anti-skid elements on the front ears or may be in lieu of anti-skid elements on the front ears.

In embodiments, the first and second anti-skid elements may be disposed as a strip or multiple strips in a generally vertical direction and may cover between approximately 25-100% of the length of the front ear. For example, the anti-skid elements may extend from substantially the top to the bottom of each front ear of the absorbent article. The strip may be limited in width so as to cover just a portion of each front ear. Moreover, the strip may be continuous or segmented.

In embodiments, the anti-skid elements comprise an elastomer with a high coefficient of friction that reduces the movement of the front waist portion relative to the back ears and/or back waist portions when the absorbent article is worn. In this manner, undesirable shifting of the absorbent article, when fastened to a wearer, is reduced.

In an exemplary embodiment, an absorbent article has a longitudinal axis and a lateral axis, and includes: a back waist portion having a first back longitudinal side edge and a second back longitudinal side edge; a first back side panel extending outward from the first back longitudinal side edge of the back waist portion; a second back side panel extending outward from the second back longitudinal side edge of the back waist portion; a front waist portion having a first front longitudinal side edge and a second front longitudinal side edge; a first front side panel extending outward from the first front longitudinal side edge of the front waist portion, the first front side panel comprising a first anti-skid element disposed on an outward-facing portion of the first front side panel and contacting an inward-facing portion of at least one of the first back side panel and the back waist portion when the absorbent article is in a fastened configuration; a second front side panel extending outward from the second front longitudinal side edge of the front waist portion, the second front side panel comprising a second anti-skid element disposed on an outward-facing portion of the second front side panel and contacting an inward-facing portion of at least one of the second back side panel and the back waist portion when the absorbent article is in a fastened configuration; and a crotch portion extending longitudinally between the front waist portion and the back waist portion.

The first anti-skid element may contact the inward-facing portion of the first back side panel and the second anti-skid element may contact the inward-facing portion of the second back side panel when the absorbent article is in a fastened configuration. The first anti-skid element may also contact the inward-facing portion of the back waist portion, and the second anti-skid element may also contact the inward-facing portion of the back waist portion.

The absorbent article may further include: a first fastening tab extending outward from the first back side panel and having a first fastening component for fastening the first fastening tab to at least one of the front waist portion and the first front side panel; and a second fastening tab extending outward from the second back side panel and having a second fastening component for fastening the second fastening tab to at least one of the front waist portion and the second front side panel.

The absorbent article may further include: a third anti-skid element disposed on an inward-facing portion of the first fastening tab such that the third anti-skid element contacts an outward-facing portion of at least one of the first waist portion and the first front side panel when the first fastening tab is in a fastened configuration; and a fourth anti-skid element disposed on an inward-facing portion of the second fastening tab such that the fourth anti-skid element contacts an outward-facing portion of at least one of the front waist portion and the second front side panel when the second fastening tab is in a fastened configuration.

In accordance with exemplary embodiments of the present invention, each of the first and second anti-skid elements has a coefficient of friction sufficient to reduce relative movement between the front waist portion and at least one of the first back side panel, the second back side panel, and the back waist portion when the absorbent article is worn. At least one of the first and second anti-skid elements may be an elastomer.

In accordance with embodiments of the present invention, at least one of the first and second anti-skid elements may extend between approximately 25-100% of the length of the front side panel on which it is disposed. In accordance with other exemplary embodiments of the present invention, at least one of the first and second anti-skid elements may extend less than the entire width of the front side panel on which it is disposed.

In other embodiments in accordance with the present invention, an absorbent article may further include a third anti-skid element disposed on an inward-facing portion of the first front side panel such that the third anti-skid element contacts the skin of a wearer of the absorbent article when the first fastening tab is in a fastened configuration; and a fourth anti-skid element disposed on an inward-facing portion of the second front side panel such that the fourth anti-skid element contacts the skin of a wearer of the absorbent article when the second fastening tab is in a fastened configuration.

In still other embodiments in accordance with the present invention, at least one of the first and second anti-skid elements may be integrally formed with its respective front side panel, the third anti-skid element may be integrally formed with the first fastening tab, and the fourth anti-skid element may be integrally formed with the second fastening tab.

In embodiments in accordance with the present invention, the first anti-skid element approximately doubles the gripping force between the first front side panel and at least one of the first back side panel and the back waist portion when the absorbent article is in a fastened configuration, and the second anti-skid element approximately doubles the gripping force between the second front side panel and at least one of the second back side panel and the back waist portion when the absorbent article is in a fastened configuration.

In another exemplary embodiment in accordance with the present invention, an absorbent article has a longitudinal axis and a lateral axis, and includes: a front waist portion having a first front longitudinal side edge and a second front longitudinal side edge; a first front side panel extending outward from the first front longitudinal side edge of the front waist portion; a second front side panel extending outward from the second front longitudinal side edge of the front waist portion; a back waist portion having a first back longitudinal side edge and a second back longitudinal side edge; a first back side panel extending outward from the first back longitudinal side edge of the back waist portion; a second back side panel extending outward from the second back longitudinal side edge of the back waist portion; a first fastening tab extending outward from the first back side panel, the first fastening tab including a first fastening component for fastening the first fastening tab to at least one of the front waist portion and the first front side panel and a first anti-skid element disposed on an inward-facing portion of the first fastening tab such that the first anti-skid element contacts an outward-facing portion of at least one of the front waist portion and the first front side panel when the first fastening tab is in a fastened configuration; a second fastening tab extending outward from the second back side panel, the second fastening tab including a second fastening component for fastening the second fastening tab to at least one of the front waist portion and the second front side panel and a second anti-skid element disposed on an inward-facing portion of the second fastening tab such that the second anti-skid element contacts an outward-facing portion of at least one of the front waist portion and the second front side panel when the second fastening tab is in a fastened configuration; and a crotch portion extending longitudinally between the front waist portion and the back waist portion.

The first anti-skid element may contact the outward-facing portion of the first front side panel and the second anti-skid element may contact the outward-facing portion of the second front side panel when the absorbent article is in a fastened configuration. The first anti-skid element may also contact the outward-facing portion of the front waist portion, and the second anti-skid element may also contact the outward-facing portion of the front waist portion.

The absorbent article may further include a third anti-skid element disposed on an outward-facing portion of the first front side panel such that the third anti-skid element contacts an inward-facing portion of at least one of the first back side panel and the back waist portion when the absorbent article is in a fastened configuration. The absorbent article may still further include a fourth anti-skid element disposed on an outward-facing portion of the second front side panel such that the fourth anti-skid element contacts an inward-facing portion of at least one of the second back side panel and the back waist portion when the absorbent article is in a fastened configuration.

In embodiments in accordance with the present invention, each of the first and second anti-skid elements has a coefficient of friction that is sufficient to reduce relative movement between the front waist portion and at least one of the first fastener tab and the second fastener tab when the absorbent article is worn. At least one of the first and second anti-skid elements may include an elastomer.

In other embodiments in accordance with the present invention, at least one of the first and second anti-skid elements may extend between approximately 25-100% of the length of the fastener tab on which it is disposed. In other embodiments in accordance with the present invention, at least one of the first and second anti-skid elements extends less than the entire width of the fastener tab on which it is disposed.

In still other embodiments in accordance with the present invention, an absorbent article may further include a third anti-skid element disposed on an inward-facing portion of the first front side panel such that the third anti-skid element contacts the skin of a wearer of the absorbent article when the first fastening tab is in a fastened configuration; and a fourth anti-skid element disposed on an inward-facing portion of the second front side panel such that the fourth anti-skid element contacts the skin of a wearer of the absorbent article when the second fastening tab is in a fastened configuration.

In yet other embodiments in accordance with the present invention, at least one of the first and second anti-skid elements may be integrally formed with its respective fastening tab, the third anti-skid element may be integrally formed with the first fastening tab, and the fourth anti-skid element may be integrally formed with the second fastening tab.

In embodiments in accordance with the present invention, at least one of the first and second anti-skid elements may include at least one strip of anti-skid material generally disposed along the longitudinal axis of an absorbent article. The strip of anti-skid material may include a continuous strip, a segmented strip, a sinusoidal-shaped strip, or a zig-zag-shaped strip. The at least one strip of anti-skid material may also include a plurality of strips of anti-skid material. The plurality of strips may be parallel to one another, and may be evenly spaced from one another.

In other embodiments in accordance with the present invention, at least one of the first and second anti-skid elements may also include at least one strip of anti-skid material that is generally disposed at a diagonal to the longitudinal axis of the absorbent article.

Other features and advantages of the present invention will become readily apparent from the following detailed description, the accompanying drawings and the appended claims.

BRIEF DESCRIPTION OF THE DRAWINGS

The above and related objects, features and advantages of the present invention will be more fully understood by reference to the following, detailed description of the preferred, albeit illustrative, embodiment of the present invention when taken in conjunction with the accompanying figures, wherein:

FIG. 2D is a plan view of the outside surface of an absorbent article according to still another exemplary embodiment of the present invention;

DETAILED DESCRIPTION OF THE PREFERRED EMBODIMENTS

As used herein, the term "absorbent article" refers to devices which absorb and contain body exudates and, more specifically, refers to devices which are placed against or in proximity to the body of the wearer to absorb and contain the various exudates discharged by the body. The term "disposable" is used herein to describe absorbent articles which are not intended to be laundered or otherwise restored or reused as an absorbent article, but instead are intended to be discarded after a single use and, preferably, to be recycled, composted or otherwise disposed of in an environmentally compatible manner.

Figure 1:
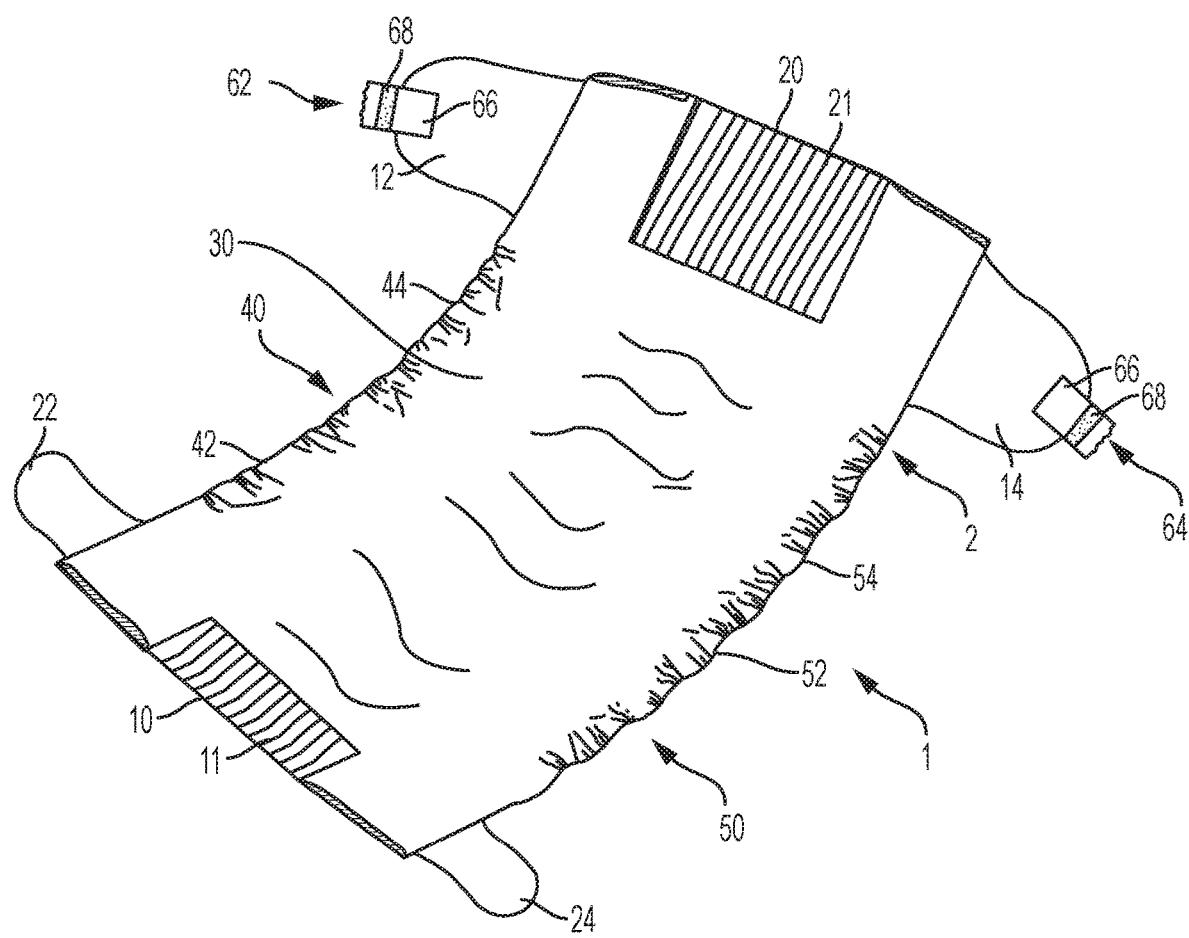
FIG. 1 is an isometric view of the inside surface of an absorbent article according to an exemplary embodiment of the present invention.

FIG. 1 is an isometric view of an inner surface of an absorbent article generally designated by reference number 1 and FIGS. 2A-2F are plan views of the outside surface of an absorbent article, according to exemplary embodiments of the present invention. In FIG. 1, the inside surface of the absorbent article 1 is facing upwards, and in FIGS. 2A-2F, the outside surface of the absorbent article 1 is facing upwards.

The absorbent article 1 may have a chassis 2 comprising a front waist portion 10, a back waist portion 20, and a crotch portion 30 extending between the front and back waist portions 10, 20. The chassis 2 has longitudinal side edges that generally run in the longitudinal direction (e.g., lengthwise) of the absorbent article 1 and lateral end edges that run between the longitudinal side edges generally in the lateral direction of the absorbent article 1.

The front waist portion 10 may include a front waist elastic 11 and the back waist portion 20 may include a back waist elastic 21. The front and back waist elastics 11, 21 provide elasticity to the waist of the absorbent article 1, so that the absorbent article 1 may have a snug fit around the wearer's waist. As is known in the art, the front and back elastics 11, 21 may be made up of one or more elongated elastic elements extending transversely from the lateral side edges of the front and back waist portion 10, 20. In other embodiments, only the front or back waist portions 10, 20 may include elasticized portions.

Elastic strands 42, 52 may be disposed along the free, side edges 44, 54 of the right and left leg area 40, 50 at crotch portion 30 to provide gathers that provide a tight fit around the wearer's crotch and thighs and serve as a barrier to guard against leakage of body exudates. The elastic strands 42, 52 may extend along the entire side edges 44, 54 of the right and left leg area 40, 50 or may extend only along a portion thereof. An alternate elastic material such as an elastic film or ribbon may be used instead of elastic strands. In exemplary embodiments, the elastic material may be used in conjunction with leg cuffs that extend longitudinally along the sides of the chassis as described in U.S. Pat. No. 8,795,250, which is incorporated herein by reference.

In a preferred embodiment, first and second back side panels, also referred to as back ears, 12, 14 are attached to and extend outward from the longitudinal side edges of the chassis 2 at the back waist portion 20. First and second front ears 22, 24 are similarly attached to and extend outward from the longitudinal side edges of the chassis 2 at the front waist portion 10. In embodiments, the back ears may be larger than the front ears so that the back ears can wrap around to the front waist portion for fastening to the wearer. Fastening components, such as fastening tabs 62, 64, may be disposed on first and second back ears 12, 14, and may extend beyond the outer side edge of the first and second back ears 12, 14. The fastening tabs 62, 64 are used to fasten the absorbent article around the waist of the wearer.

The fastening tabs 62, 64 may include a base layer 66 and a fastener element 68. The base layer 66 may be, for example, a nonwoven material layer or a polymeric material layer. The base layer 66 may be attached to the first or second side back ear 12, 14 by any known attachment method, for example, adhesive, ultrasonic bonding, thermal bonding, or the like. Fastener element 68 may be any suitable type of mechanical fastener, for example, tapes, adhesives, hook fasteners, loop fasteners, snap fasteners, buttons, or the like. The fastener element 68 may attach to a landing zone or cooperating fastener 69 on the front waist portion 10, or alternatively on the first front ear 22 or second front ear 24. For example, in the case of a hook fastener, the landing zone or cooperating fastener 69 may be a strip of loop material or nonwoven material. However, the fastener element 68 may also be adapted to engage directly with an outer nonwoven surface of the front waist portion 10 or the first or second front ears 22, 24, and thus may not require a landing zone or cooperating fastener.

Figure 2A:
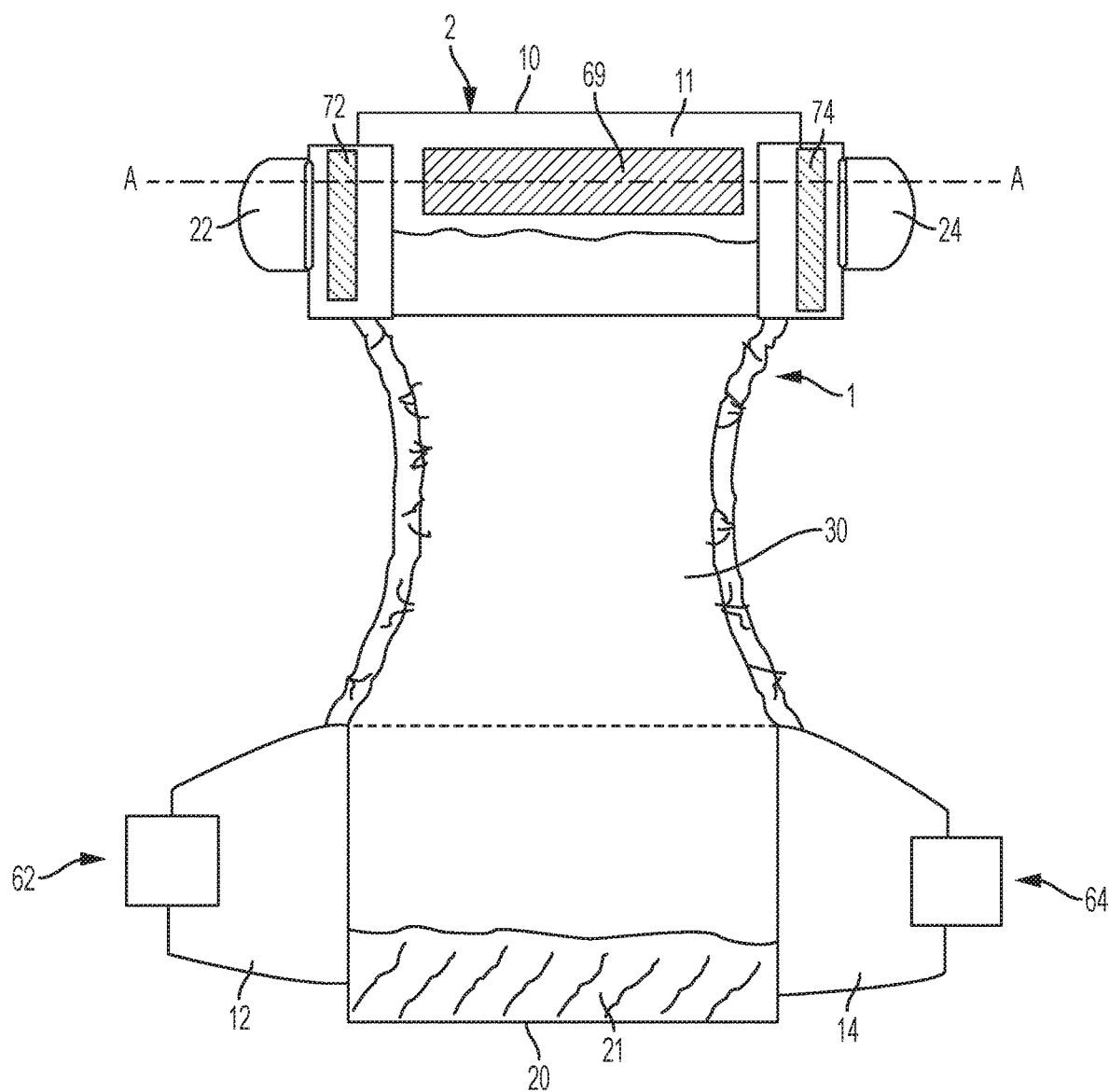
FIG. 2A is a plan view of the outside surface of an absorbent article according to an exemplary embodiment of the present invention.
Figure 2B:
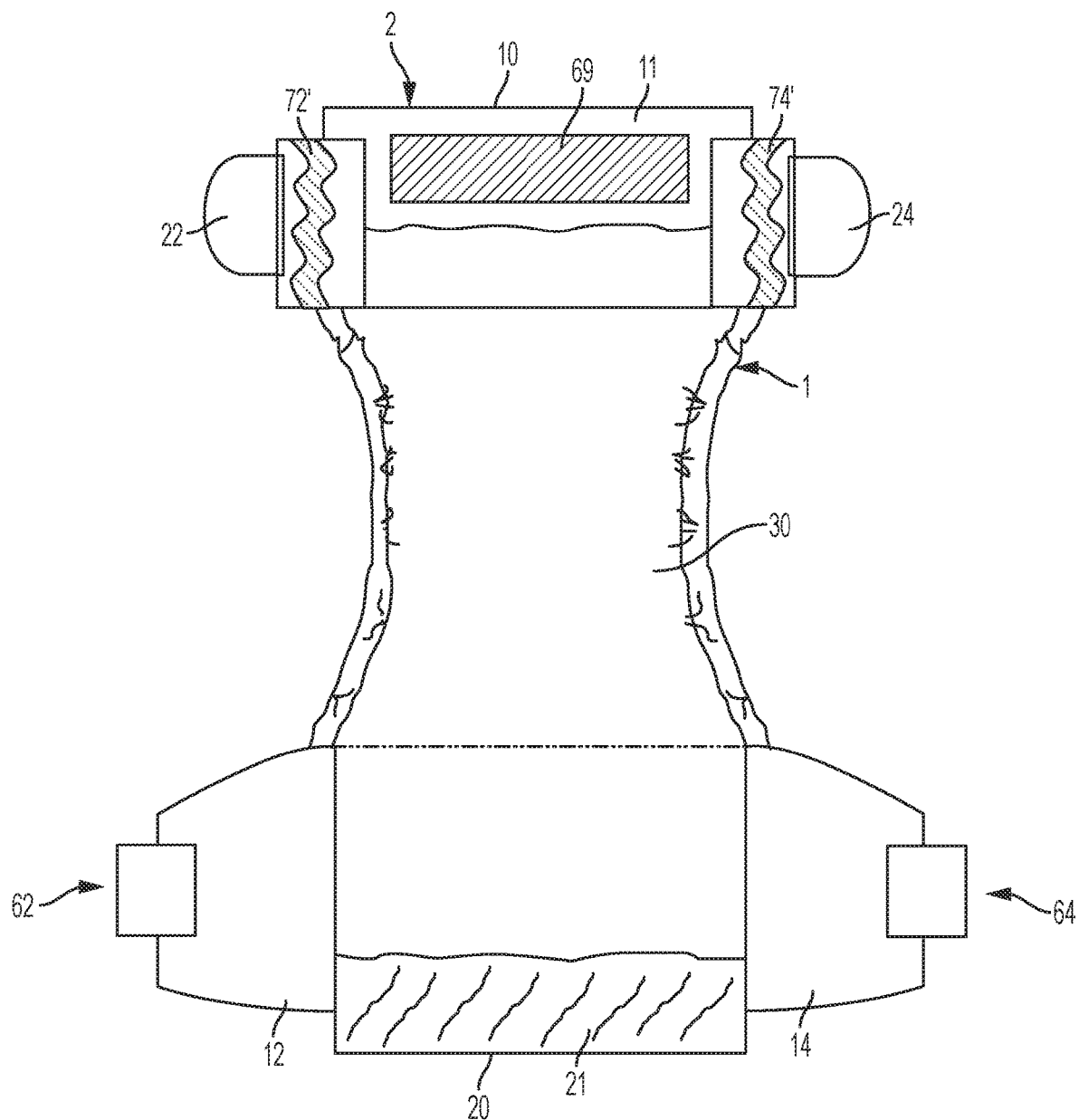
FIG. 2B is a plan view of the outside surface of an absorbent article according to another exemplary embodiment of the present invention.
Figure 2C:
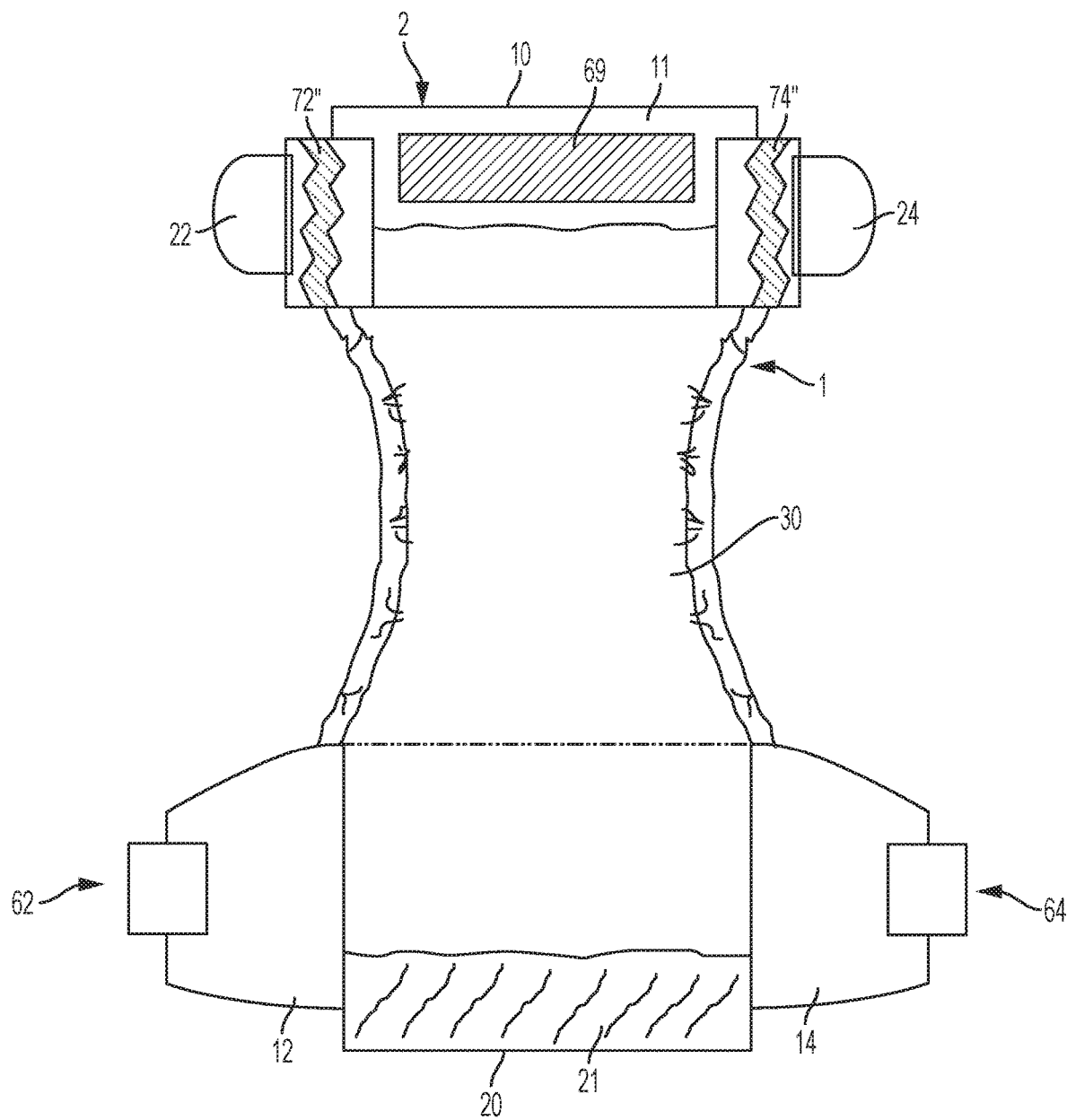
FIG. 2C is a plan view of the outside surface of an absorbent article according to yet another exemplary embodiment of the present invention.

The absorbent article, according to an exemplary embodiment, further comprises a first anti-skid element 72 disposed along at least an outward-facing portion of the first front ear 22 and a second anti-skid element 74 disposed along at least an outward-facing portion of the second front ear 24. The anti-skid elements 72, 74 are designed to achieve friction between the outside surface of the front ears and the inside surfaces of the corresponding back ears or back waist portion to minimize the shifting of the absorbent article on a wearer when worn. In an exemplary embodiment, the first and second anti-skid elements 72, 74 are disposed in a generally vertical direction from substantially the top to the bottom of the first and second front ears 22, 24. Moreover, one or both of the anti-skid elements 72, 74 may extend the entire width of the respective front ear 22, 24 or may be limited in width, with a smaller width in the case of a typical baby diaper or a larger width in the case of an adult diaper. In some embodiments, the anti-skid elements may be disposed in straight lines, as illustrated in FIG. 2A. In alternative embodiments, the anti-skid elements may be disposed, for example, in other shapes or in patterns, such as in a sinusoidal shape or as a zig-zag shape in a generally vertical direction on the first and second front ears 22, 24. FIG. 2B shows an example of an alternative embodiment with sinusoidally-shaped anti-skid elements 72', 74'. FIG. 2C shows an alternative embodiment with zig-zag-shaped anti-skid elements 72", 74". In embodiments, the anti-skid material may be applied or formed integrally with the absorbent article.

The embodiments in accordance with the present invention that are shown in FIGS. 1 and 2A-2C include elastics. However, embodiments in accordance with the present invention do not have to include elastics.

Figure 2E:
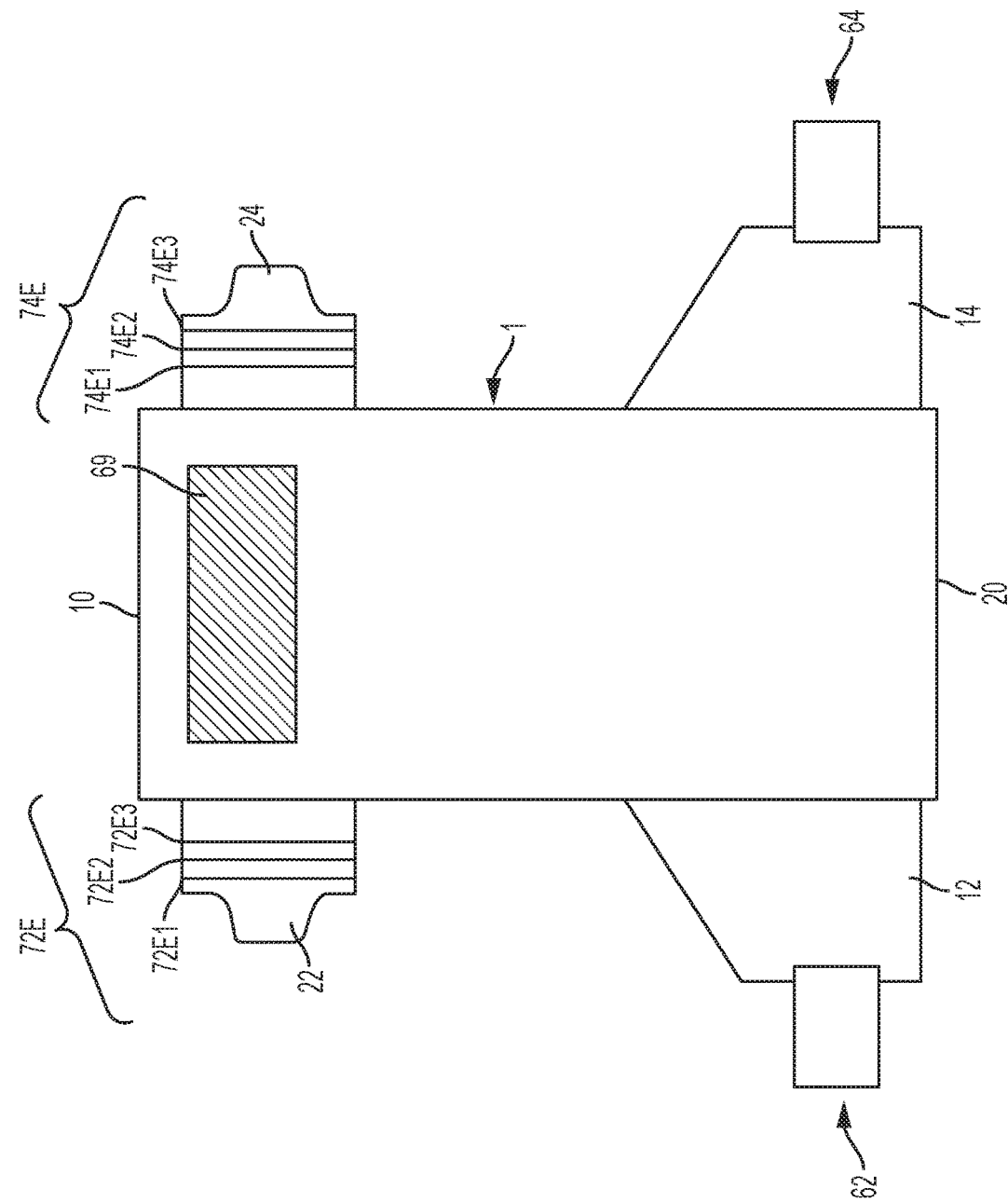
FIG. 2E is a plan view of the outside surface of an absorbent article according to a further exemplary embodiment of the present invention.
Figure 2F:
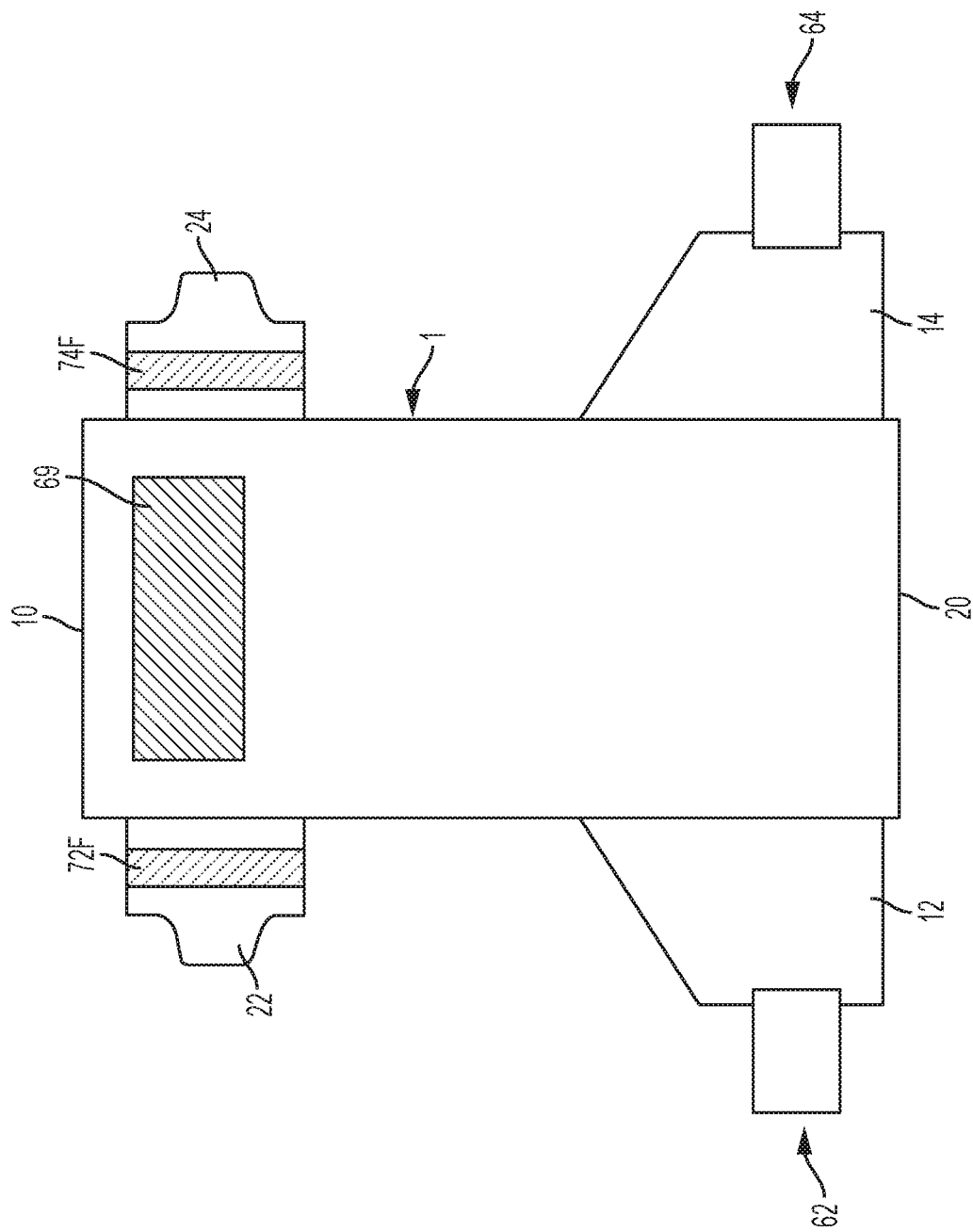
FIG. 2F is a plan view of the outside surface of an absorbent article according to a still further exemplary embodiment of the present invention.

FIGS. 2D to 2F show plan views of various alternative embodiments of anti-skid elements on the outward-facing portions of the front ears 22, 24 of an absorbent article in accordance with different embodiments of the present invention. The embodiments shown in FIGS. 2D-2F may or may not include elastics. For ease of understanding, the elastics are not shown in these embodiments.

In the embodiment of FIG. 2D, which shows a plan view of an absorbent article laid flat down on its inside surface, anti-skid elements 72D, 74D are formed as a single strip on the outside surface of each of the front ears, similar to the placement of the anti-skid elements 72, 74 in the embodiment shown in FIG. 2A.

FIG. 2E shows an alternative embodiment that varies from FIG. 2D in that the anti-skid elements 72E, 74E on front ears 22, 24 of the absorbent article are shown as each formed of a series of three, substantially parallel strands 72E1, 72E2, 72E3, 74E1, 74E2, and 74E3 extending substantially vertically near the edge of the front ears. These strands may be evenly or unevenly spaced from one another and may be of equal or unequal width.

FIG. 2F shows another embodiment of the absorbent article in which each of the front ears of the absorbent article includes an anti-skid element 72F, 74F that has diagonal stripes of anti-skid material formed along the length of the respective anti-skid strip.

Figure 2G:
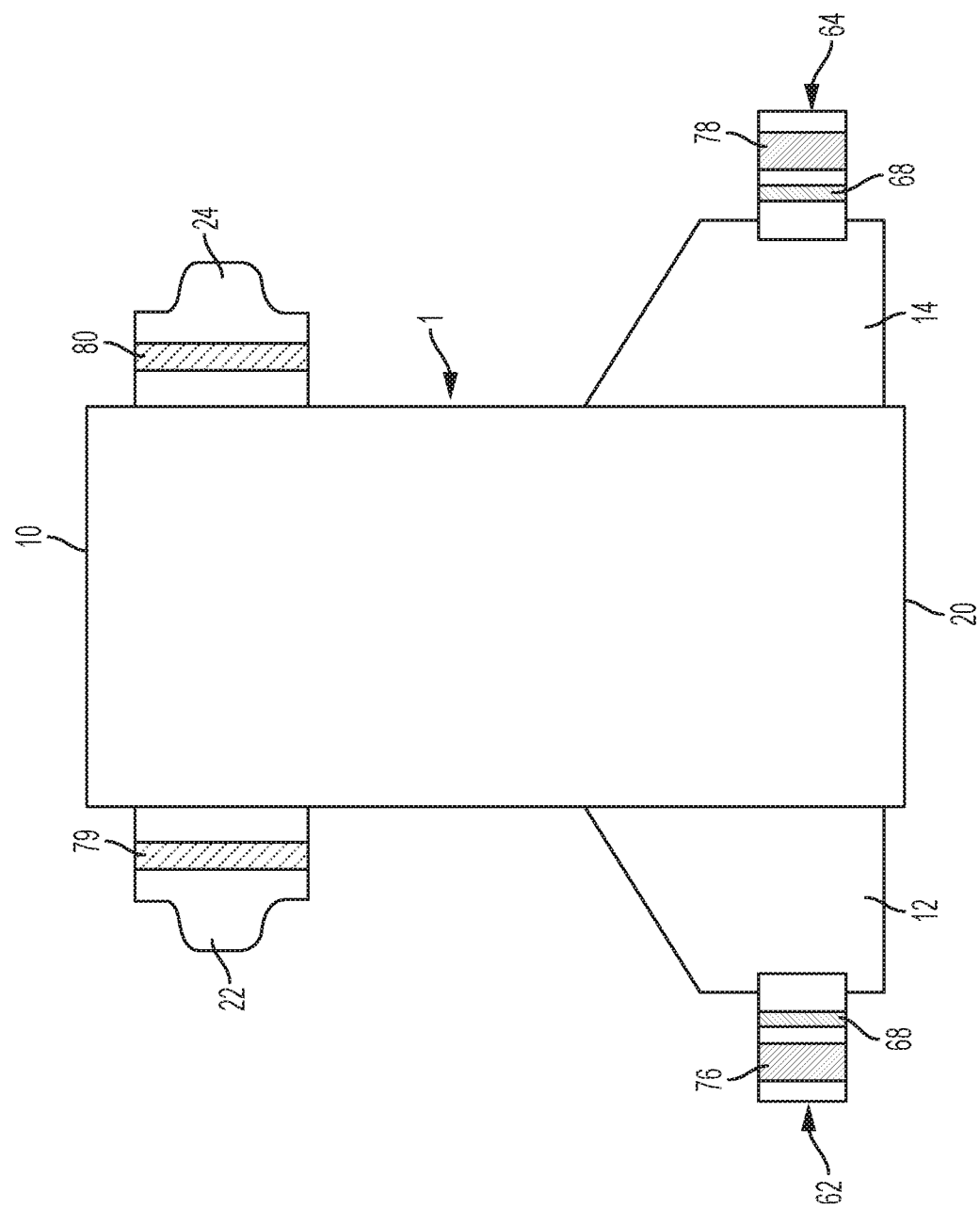
FIG. 2G is a plan view of the inside surface of an absorbent article according to another exemplary embodiment of the present invention.

FIG. 2G shows an inside surface of an embodiment of the absorbent article according to the present invention. In this embodiment, an anti-skid element 76, 78 may be formed on the inside surface of each of respective fastening tabs 62, 64 to prevent undesirable shifting of the absorbent article when worn. The anti-skid elements 76, 78 are present in addition to fastener elements 68 on the fastening tabs. Anti-skid elements 76, 78 may exist in conjunction with any variation of anti-skid elements on the outside surface of the front ears, such as in the embodiments shown in FIGS. 2A-2F. Alternatively, anti-skid elements 76, 78 may be used in lieu of the anti-skid elements on the front ears. Alternatively, or in addition, to one or more of the anti-skid elements 72, 74, 76, 78, anti-skid elements 79, 80 may be included on the inside surface of front ears 22, 24 to achieve friction between the inside surface of the front ears and the wearer to minimize the shifting of the absorbent article on a wearer when worn.

While certain variations of the anti-skid elements have been shown in the above figures, the anti-skid elements according to the present invention are not limited to any one of the illustrated embodiments.

The anti-skid elements may generally extend between approximately 25% and 100% of the length of a front ear 22 or 24 or of fastening tabs and may generally cover between approximately 10% to 100% of the area of an outside and/or inside surfaces of a front ear 22 or 24 or the inside surface of fastening tabs 62, 64. In an exemplary embodiment, the anti-skid elements may preferably be between approximately 5 to 25 mm wide (which may depend on the size of the absorbent article) and cover between approximately 25-100% of the length of the outside and/or inside surfaces of a front ear or the inside surface of a fastening tab.

Anti-skid elements may be formed integrally with front ear or fastening tab material or may be attached to the front ears or fastening tabs, such as with adhesive, ultrasonic or other bonding methods. The front ears or fastening tabs themselves can be attached to the main diaper chassis or may be integral to the body of the article In embodiments, the anti-skid elements (or variations thereof) comprise a non-skid material, such as a Kraton® elastomer from Kraton Polymers LLC of Houston, Tex., USA or another high coefficient of friction material, that is applied to a surface, such as the outer-facing or inner-facing surface of the front ears, i.e., facing a wearer's outer garment that covers the absorbent article or facing the wearer's skin, or the inner-facing surface of the fastening tabs.

The anti-skid elements themselves preferably do not comprise hooks or other fastening elements that attach to other surfaces.

Figure 3:
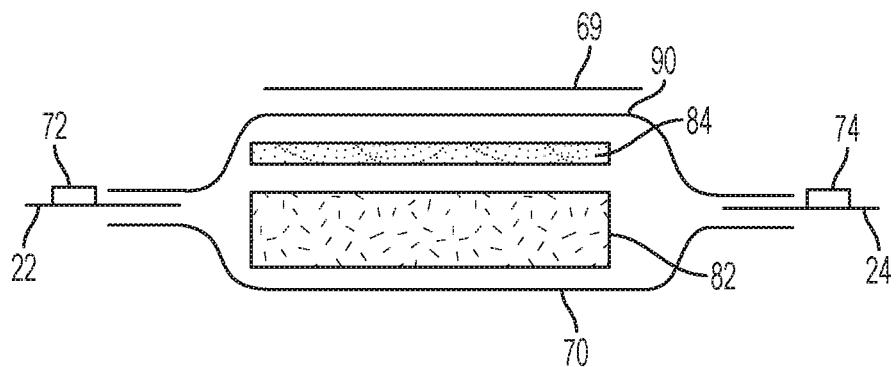
FIG. 3 is a cross-sectional view taken along line A-A of FIG. 2A.
Figure 4:
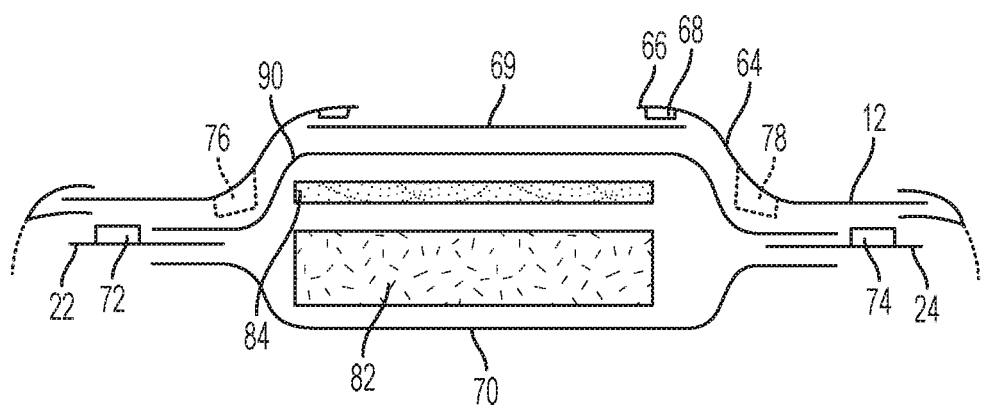
FIG. 4 is a simplified top view of a front waist portion of an absorbent article in a fastened configuration according to an exemplary embodiment of the present invention.
Figure 5:
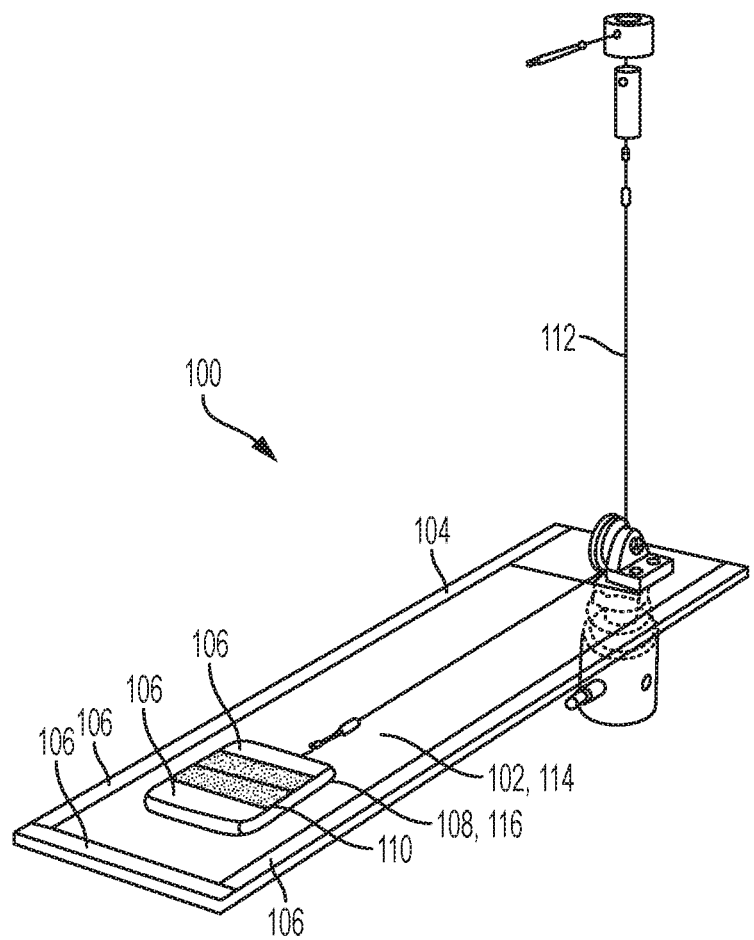
FIG. 5 is a schematic diagram of a test system used to measure the gripping forces and coefficients of friction present in absorbent articles.

FIG. 3 shows a cross-sectional view of an embodiment of absorbent article 1, taken along line A-A of FIG. 2A, and in particular shows a cross-section of the front waist portion 10 of the chassis 2 with the first and second front ears 22, 24, fastening tabs 62, 64, anti-skid elements 72, 74 and landing zone 69. FIG. 3 also illustrates a possible layered structure of chassis 2 including a backsheet 70, a topsheet 90, an absorbent core 82 disposed between the backsheet 70 and topsheet 90, and an acquisition/distribution layer (ADL) 84 that is disposed between the absorbent core 82 and the topsheet 90. The back and front ears 12, 14, 22, 24 may be attached to the respective portions of the back waist portion and front waist portion 20, 10 between the backsheet 70 and topsheet 90, as shown in FIG. 4, generally with no absorbent core 82 or ADL 84 therebetween. In embodiments, one or both of the pairs of front and back ears 12, 14, 22, 24 may be formed integrally from the backsheet 70 or topsheet 90

In an example embodiment in which the absorbent article is in a diaper configuration, as shown in FIG. 4, the absorbent article 1 may be secured around a wearer's waist by attaching the fastening tabs 62, 64 of the first and second back ears 12, 14 to the front waist portion 10. The position at which the fastening tabs 62, 64 are attached the front waist portion 10 may vary due to, for example, the different possible waist sizes of potential users of the diaper as well as due to the size and configuration of the diaper. Thus, when anti-skid components 72, 74 are present, the outside surface (e.g., backsheet 70) of the first and second anti-skid components 72, 74 on the front ears 22, 24 will come into enhanced frictional contact with the inside surfaces of either the back ears 12, 14, back waist portion 20, or both. In any event, when the diaper is in a fastened configuration, the relatively high coefficient of friction of the outside surface of the anti-skid elements 72, 74 will restrict the undesirable shifting of the diaper so that the article generally fits better on the wearer. In the embodiment illustrated in this figure, anti-skid elements 76, 78 on fastening tabs are shown as optional with dashed lines. When present, anti-skid elements 76, 78 will also restrict the undesirable shifting of the diaper.

Topsheet 90 may be made of any suitable relatively liquid-pervious material currently known in the art or later discovered that permits passage of a liquid therethrough. The topsheet 90 typically comes in contact with the skin of the wearer, and is preferably made of a material that is gentle to human skin. Examples of suitable topsheet materials include nonwoven, spun-bonded or carded webs of polypropylene, polyethylene, nylon, polyester and blends of these materials, or perforated, apertured or reticulated films, and the like. Nonwoven materials are exemplary because such materials readily allow the passage of liquids to the underlying acquisition/distribution layer 84, and therethrough to absorbent core 82. The topsheet 90 is preferably formed of a single ply of nonwoven material that may be made of fibers comprising polypropylene, polyethylene, polyethylene terephthalate (PET), polylactide (PLA), nylon, polyester and blends of these materials which have been thermally bonded, spunbonded, spunlaced, hydroentangled, or a combination thereof, or a composite of nonwoven material, such as a spunbond-meltblown-spunbond (SMS) nonwoven. For example, the nonwoven material may have a basis weight of about 8-30 grams per square meter and have appropriate strength and softness for use as a topsheet in an application which will be in contact with human skin. Topsheet 90 may be treated with a surfactant, over the whole surface or a portion of the surface, rendering it hydrophilic to facilitate the passage of moisture through topsheet 90 and into the acquisition/distribution layer 84 and the absorbent core 82. The present invention is not intended to be limited to any particular material for topsheet 90 and other topsheet materials will be readily apparent to those skilled in the art.

Acquisition/distribution layer 84 may be a single layer or multiple layers made of synthetic or natural material, or a combination of both, or a single multilayer apertured film. Acquisition/distribution layer 84 serves to quickly collect and distribute discharged body fluid to absorbent core 82. Because such fluid is typically discharged in gushes, the area of absorbent core 82 proximate to the point of fluid discharge may be overwhelmed by its rate, resulting in a leak. Therefore, the acquisition/distribution layer 84 facilitates transport of the fluid from the point of discharge across its surface area to contact other parts of absorbent core 82 from which it can be more readily absorbed. The use of an acquisition/distribution layer is well known in the art. Accordingly, acquisition/distribution layer 84 of the absorbent article 1 may have any well known or as yet undiscovered construction.

Absorbent core 82 may be any absorbent material which is capable of absorbing and retaining liquids such as urine and certain other body exudates to help prevent the liquid from either rewetting the wearer or otherwise leaking out of the absorbent article. The absorbent material may generally be compressible, conformable to the shape of the wearer's body and should not impede normal movement by the wearer. The absorbent core 82 may be manufactured in a wide variety of sizes and shapes, (e.g., rectangular, hourglass, "T"-shaped, asymmetric, etc.) and from a wide variety of liquid-absorbent materials commonly used in disposable diapers and other absorbent articles. Examples of suitable absorbent materials include wood pulp fluff, creped cellulose wadding, meltblown polymers, chemically stiffened, modified or cross-linked cellulosic fiber, tissue including tissue wraps and tissue laminates, absorbent foams, absorbent sponges, superabsorbent polymers (SAP), absorbent gelling materials, or any similar absorbent material or combinations of materials.

The configuration and construction of absorbent core 82 may also be varied. For example, the absorbent core may have varying caliper zones, a hydrophilic gradient, an absorbent gelling material gradient, or lower average density and lower average basis weight acquisition zones, or may comprise one or more layers or structures (e.g., sheets or webs). In addition, each layer need not be formed of a single unitary piece of material, but may be formed of a number of smaller strips or components joined together lengthwise or widthwise, as long as they are in fluid communication with one another. The total absorbent capacity of absorbent core 82 should, however, be compatible with the design loading and the intended use of the absorbent article 1. Further, the size and absorbent capacity of the absorbent core 82 may be varied to accommodate wearers ranging from infants through adults.

Backsheet 70 may be made of a liquid impermeable material or be comprised of multiple layers in which one layer is liquid impermeable. For example, the backsheet 70 may be comprised of an inner layer of film that is suitably pliable and liquid impervious and an outer layer of a liquid and/or vapor-pervious material. Typical materials for the inner layer of the backsheet 70 include films of polyethylene, polypropylene, polyester, nylon and polyvinyl chloride (PVC) and blends of these materials. For example, the inner layer may be made of a polyethylene film having a thickness in the range of about 0.4 to 2.0 mils. Other inner layer materials may be readily apparent to those skilled in the art. Inner layer of backsheet 70 preferably has sufficient liquid imperviousness to prevent any leakage of fluids. The outer layer of the backsheet 70 may be made of a liquid and/or vapor-pervious material which may be selected from the same group of materials from which the topsheet was selected. The outer layer may have a basis weight of, for example, between about 5-45 grams per square meter. Unlike topsheet 90, however, the material used for the outer layer of the backsheet 70 is preferably rendered hydrophobic by omitting the surfactant discussed above with respect to topsheet 90. The outer layer of the backsheet 70 may be manufactured by well known methods such as thermal bonding, chemical bonding, spun bonding and hydroentanglement, or by a combination of spun bonding and hydroentanglement.

The first and second front ears 22, 24 and first and second back ears 12, 14 may be made of a nonwoven, a film, or a combination thereof. The first and second front ears 22, 24 and the first and second ears 12, 14 may be made to vary breathability to air and/or moisture vapor, elasticity, fluid permeability, softness, or any other desired characteristic depending on the particular materials and construction used to form the ears. In some example embodiments, the first and second front ears 22, 24 and/or the first and second back ears 12, 14 may be made of a non-elastic material, an elastic material stretchable in any direction or a combination thereof. In some example embodiments, the first and second front ears 22, 24 may include indicia for providing instruction in applying the absorbent article.

An absorbent article in accordance with embodiments of the present invention has been shown to achieve a significant improvement toward eliminating the shifting of the absorbent article while it is being worn. Specifically, the gripping force of a control sample of a front ear of a conventional absorbent article was compared to the gripping force of a high-coefficient-of-friction (high-CoF) sample of a front ear of an absorbent article in accordance with the present invention. The high-CoF front ear sample in accordance with the present invention was shown to provide at least twice the gripping force, and hence twice the coefficient of friction, of the control front ear sample of the conventional absorbent article.

The control front ear sample was made from a 30 gsm, SMS nonwoven, PILLOW BOND material manufactured by First Quality Nonwovens, Inc. and bearing identification number NWN0213. The control front ear sample had a length of 65 mm and a width of 45 mm.

The high-CoF front ear sample was made from a 40 gsm, SMS nonwoven, PILLOW BOND material bearing the First Quality Baby Products. The high-CoF front ear sample also had a length of 65 mm and a width of 45 mm. The high-CoF front ear sample further included a strip of anti-skid material having a length of 65 mm (i.e., the strip extended the entire length of the high CoF sample) and a width of 10 mm. The anti-skid material was an elastomer manufactured by Velcro Companies and bearing identification number CFM #41-8206.

The control sample and the high-CoF sample were both tested on a Model No. 3343/Q7066 Test System equipped with Bluehill® Software, a Model No. 2810-005 Coefficient of Friction Fixture (including pull cord, friction table, and a friction sled weighing 200 g), and a load cell having an appropriate rating for the forces to be measured during the testing. All of the equipment used during the testing is manufactured by INSTRON®. The testing was performed in accordance with First Quality Baby Products Document No. FQB PD-063.0, the contents of which are incorporated by reference herein in their entirety.

A schematic drawing of the test system 100 is shown in FIG. 6. In a first portion of the testing, a sample of an elastic back ear material 102 was secured onto the friction table 104 of the test system 100 in an absolutely flat position using tape 106. The sample of back ear material 102 was made from an EFT elastic laminate manufactured by APLIX® and bearing product number AH21R0150L01034X0245.

The control sample of front ear material 108 was then secured to the friction sled 110 using tape 106. The types of tape that may used to tape the samples of the back ear and front ear materials 102, 108 to, respectively, the friction table 104 and the friction sled 110 are well known to persons of ordinary skill in the art and thus will not be described further herein.

Next, the friction sled 110 was attached to the pull cord 112 and was placed at a starting position on the friction table 104. This placement of the friction sled 104 was done very lightly and gently so as to prevent any unnatural bond from developing between the two samples 102, 108. Once it was determined that the pull cord 112 was taut, the test was performed in accordance with the instructions provided by the Bluehill® Software by pulling the friction sled 110 along the friction table 104 at a speed of 150 mm/minute. The testing was performed on a total of five samples each of the control front ear material 108 and the elastic back ear material 102.

The testing of the control sample of the front ear material 108 was also performed against a sample of a material 114 used in nonwoven cuffs and inner lateral edges of absorbent articles. The sample of this cuff material 114 was made from a 15 gsm, SMS nonwoven material manufactured by First Quality Nonwovens, Inc. and bearing identification number NWN0743. As with the testing involving the elastic back ear material 102, the testing was performed on a total of five samples of the control front ear material 108 and the cuff material 114.

The above described testing was then repeated for the high-CoF front ear sample 116 against both the elastic back ear material 102 and the cuff material 114 identified above. A summary of the results of the testing appears below in Tables 1 and 2.

TABLE 1

Averaged Static Force (gf)

|  | Elastic Back Ear Material | Cuff Material |
| --- | --- | --- |
| Control Front Ear Material | 120 | 60 |
| High-CoF Front Ear Material | 220 | 120 |

TABLE 2

Averaged Kinetic Force (gf)

|  | Elastic Back Ear Material | Cuff Material |
| --- | --- | --- |
| Control Front Ear Material | 90 | 60 |
| High-CoF Front Ear Material | 220 | 120 |

As shown in Tables 1 and 2, based on the averaged results of the five test samples for each combination of materials tested, the high-CoF front ear samples 116 in accordance with the embodiments of the present invention exhibited at least twice the gripping force (and hence at least twice the coefficient of friction) of the control samples of the front ear 108. Specifically, the high-CoF front ear sample 116 exhibited 220 gf of averaged kinetic force relative to the elastic back ear material 102, as compared to only 90 gf for the control sample of the front ear 108 (i.e., 2.4 times greater gripping force). Likewise, the high-CoF front ear sample 116 exhibited 120 gf of averaged kinetic force relative to the cuff material 114, as compared to only 60 gf for the control sample of the front ear 108 (i.e., 2 times greater gripping force).

The inventors have further determined that the increase in gripping force and coefficient of friction exhibited by absorbent articles in accordance with embodiments of the present invention is unaffected by the aging of those absorbent articles.

Now that embodiments of the present invention have been shown and described in detail, various modifications and improvements thereon can become readily apparent to those skilled in the art. Accordingly, the exemplary embodiments of the present invention, as set forth above, are intended to be illustrative, not limiting. The spirit and scope of the present invention is to be construed broadly.

What is claimed is:

1. An absorbent article having a longitudinal axis and a lateral axis, said absorbent article comprising:
   a back waist portion having a first back longitudinal side edge and a second back longitudinal side edge;
   a first back side panel attached to and extending outward from the first back longitudinal side edge of the back waist portion;
   a second back side panel attached to and extending outward from the second back longitudinal side edge of the back waist portion;
   a front waist portion having a first front longitudinal side edge and a second front longitudinal side edge;
   a first front side panel attached to and extending outward from the first front longitudinal side edge of the front waist portion, the first front side panel comprising a first anti-skid element disposed on an outward-facing portion of the first front side panel and contacting an inward-facing portion of at least one of the first back side panel and the back waist portion when the absorbent article is in a fastened configuration, the first anti-skid element being spaced laterally outwardly from the first front longitudinal side edge of the front waist portion so that the first anti-skid element does not overlap the first front longitudinal side edge of the front waist portion;
   a second front side panel attached to and extending outward from the second front longitudinal side edge of the front waist portion, the second front side panel comprising a second anti-skid element disposed on an outward-facing portion of the second front side panel and contacting an inward-facing portion of at least one of the second back side panel and the back waist portion when the absorbent article is in a fastened configuration, the second anti-skid element being spaced laterally outwardly from the second front longitudinal side edge of the front waist portion so that the second anti-skid element does not overlap the second front longitudinal side edge of the front waist portion;
   a crotch portion extending longitudinally between the front waist portion and the back waist portion,
   a first fastening tab extending outward from the first back side panel and comprising a first fastening component for fastening the first fastening tab to at least one of the front waist portion and the first front side panel;
   a second fastening tab extending outward from the second back side panel and comprising a second fastening component for fastening the second fastening tab to at least one of the front waist portion and the second front side panel;
   a third anti-skid element disposed on an inward-facing portion of the first fastening tab such that the third anti-skid element contacts an outward-facing portion of at least one of the front waist portion and the first front side panel when the first fastening tab is in a fastened configuration, the entire third anti-skid element positioned closer to an outer lateral end of the first fastening tab than the first fastening component; and
   a fourth anti-skid element disposed on an inward-facing portion of the second fastening tab such that the fourth anti-skid element contacts an outward-facing portion of at least one of the front waist portion and the second front side panel when the second fastening tab is in a fastened configuration, the entire fourth anti-skid element positioned closer to an outer lateral end of the second fastening tab than the second fastening component,
   wherein the first, second, third and fourth anti-skid elements comprise an elastomer.

2. The absorbent article of claim 1, wherein the first anti-skid element contacts the inward-facing portion of the first back side panel and the second anti-skid element contacts the inward-facing portion of the second back side panel when the absorbent article is in a fastened configuration.

3. The absorbent article of claim 2, wherein the first anti-skid element also contacts the inward-facing portion of the back waist portion.

4. The absorbent article of claim 2, wherein the second anti-skid element also contacts the inward-facing portion of the back waist portion.

5. The absorbent article of claim 1, wherein each of the first and second anti-skid elements has a coefficient of friction sufficient to reduce relative movement between the front waist portion and at least one of the first back side panel, the second back side panel, and the back waist portion when the absorbent article is worn.

6. The absorbent article of claim 1, wherein at least one of the first and second anti-skid elements extends between approximately 25-100% of the length of the front side panel on which it is disposed.

7. The absorbent article of claim 1, wherein at least one of the first and second anti-skid elements extends less than the entire width of the front side panel on which it is disposed.

8. The absorbent article of claim 1, wherein at least one of the first and second anti-skid elements comprises at least one strip of anti-skid material extending generally in alignment with the longitudinal axis of the absorbent article.

9. The absorbent article of claim 8, wherein the at least one strip comprises a continuous strip of anti-skid material.

10. The absorbent article of claim 8, wherein the at least one strip comprises a segmented strip of anti-skid material.

11. The absorbent article of claim 8, wherein the at least one strip comprises a sinusoidal-shaped strip of anti-skid material.

12. The absorbent article of claim 8, wherein the at least one strip comprises a zig-zag-shaped strip of anti-skid material.

13. The absorbent article of claim 8, wherein the at least one strip of anti-skid material comprises a plurality of strips of anti-skid material.

14. The absorbent article of claim 13, wherein the plurality of strips of anti-skid material are parallel to one another.

15. The absorbent article of claim 13, wherein the plurality of strips of anti-skid material are evenly spaced from one another.

16. The absorbent article of claim 1, wherein at least one of the first and second anti-skid elements comprises at least one strip of anti-skid material generally disposed at a diagonal to the longitudinal axis of the absorbent article.

17. The absorbent article of claim 1, further comprising:
a fifth anti-skid element disposed on an inward-facing portion of the first front side panel such that the third anti-skid element contacts the skin of a wearer of the absorbent article when the first fastening tab is in a fastened configuration;
a sixth anti-skid element disposed on an inward-facing portion of the second front side panel such that the fourth anti-skid element contacts the skin of a wearer of the absorbent article when the second fastening tab is in a fastened configuration.

18. The absorbent article of claim 1, wherein at least one of the first and second anti-skid elements is integrally formed with its respective front side panel.

19. The absorbent article of claim 1, wherein the third anti-skid element is integrally formed with the first fastening tab.

20. The absorbent article of claim 1, wherein the fourth anti-skid element is integrally formed with the second fastening tab.

21. The absorbent article of claim 1, wherein the first anti-skid element approximately doubles the gripping force between the first front side panel and at least one of the first back side panel and the back waist portion when the absorbent article is in a fastened configuration.

22. The absorbent article of claim 1, wherein the second anti-skid element approximately doubles the gripping force between the second front side panel and at least one of the second back side panel and the back waist portion when the absorbent article is in a fastened configuration.

23. An absorbent article having a longitudinal axis and a lateral axis, said absorbent article, comprising:
a front waist portion having a first front longitudinal side edge and a second front longitudinal side edge;
a first front side panel attached to and extending outward from the first front longitudinal side edge of the front waist portion;
a second front side panel attached to and extending outward from the second front longitudinal side edge of the front waist portion;
a back waist portion having a first back longitudinal side edge and a second back longitudinal side edge;
a first back side panel attached to and extending outward from the first back longitudinal side edge of the back waist portion;
a second back side panel attached to and extending outward from the second back longitudinal side edge of the back waist portion;
a first fastening tab attached to and extending outward from the first back side panel, the first fastening tab comprising a first fastening component for fastening the first fastening tab to at least one of the front waist portion and the first front side panel and a first anti-skid element disposed on an inward-facing portion of the first fastening tab such that the first anti-skid element contacts an outward-facing portion of at least one of the front waist portion and the first front side panel when the first fastening tab is in a fastened configuration, the first anti-skid element being spaced laterally outwardly from the first back longitudinal side edge of the back waist portion so that the first anti-skid element does not overlap the first back longitudinal side edge of the back waist portion, the entire first anti-skid element positioned closer to an outer lateral end of the first fastening tab than the first fastening component;
a second fastening tab attached to and extending outward from the second back side panel, the second fastening tab comprising a second fastening component for fastening the second fastening tab to at least one of the front waist portion and the second front side panel and a second anti-skid element disposed on an inward-facing portion of the second fastening tab such that the second anti-skid element contacts an outward-facing portion of at least one of the front waist portion and the second front side panel when the second fastening tab is in a fastened configuration, the second anti-skid element being spaced laterally outwardly from the second back longitudinal side edge of the back waist portion so that the second anti-skid element does not overlap the second back longitudinal side edge of the back waist portion, the entire second anti-skid element positioned closer to an outer lateral end of the second fastening tab than the second fastening component; and
a crotch portion extending longitudinally between the front waist portion and the back waist portion,
wherein the first and second anti-skid elements comprise an elastomer.

24. The absorbent article of claim 23, wherein the first anti-skid element contacts the outward-facing portion of the first front side panel and the second anti-skid element contacts the outward-facing portion of the second front side panel when the absorbent article is in a fastened configuration.

25. The absorbent article of claim 23, wherein the first anti-skid element also contacts the outward-facing portion of the front waist portion.

26. The absorbent article of claim 23, wherein the second anti-skid element also contacts the outward-facing portion of the front waist portion.

27. The absorbent article of claim 23, further comprising a third anti-skid element disposed on an outward-facing portion of the first front side panel such that the third anti-skid element contacts an inward-facing portion of at least one of the first back side panel and the back waist portion when the absorbent article is in a fastened configuration.

28. The absorbent article of claim 27, wherein the third anti-skid element is integrally formed with the first front side panel.

29. The absorbent article of claim 27, further comprising a fourth anti-skid element disposed on an outward-facing portion of the second front side panel such that the fourth anti-skid element contacts an inward-facing portion of at least one of the second back side panel and the back waist portion when the absorbent article is in a fastened configuration, wherein the fourth anti-skid element is integrally formed with the second front side panel.

30. The absorbent article of claim 23, wherein each of the first and second anti-skid elements has a coefficient of friction sufficient to reduce relative movement between the front waist portion and at least one of the first fastener tab and the second fastener tab when the absorbent article is worn.

31. The absorbent article of claim 23, wherein at least one of the first and second anti-skid elements extends between approximately 25-100% of the length of the fastener tab on which it is disposed.

32. The absorbent article of claim 23, wherein at least one of the first and second anti-skid elements comprises at least one strip of anti-skid material extending generally in alignment with the longitudinal axis of the absorbent article.

33. The absorbent article of claim 32, wherein the at least one strip comprises a continuous strip of anti-skid material.

34. The absorbent article of claim 32, wherein the at least one strip comprises a segmented strip of anti-skid material.

35. The absorbent article of claim 32, wherein the at least one strip comprises a sinusoidal-shaped strip of anti-skid material.

36. The absorbent article of claim 32, wherein the at least one strip comprises a zig-zag-shaped strip of anti-skid material.

37. The absorbent article of claim 32, wherein the at least one strip of anti-skid material comprises a plurality of strips of anti-skid material.

38. The absorbent article of claim 37, wherein the plurality of strips of anti-skid material are parallel to one another.

39. The absorbent article of claim 37, wherein the plurality of strips of anti-skid material are evenly spaced from one another.

40. The absorbent article of claim 23, wherein at least one of the first and second anti-skid elements comprises at least one strip of anti-skid material generally disposed at a diagonal to the longitudinal axis of the absorbent article.

41. The absorbent article of claim 23, further comprising:
a third anti-skid element disposed on an inward-facing portion of the first front side panel such that the third anti-skid element contacts the skin of a wearer of the absorbent article when the first fastening tab is in a fastened configuration; and
a fourth anti-skid element disposed on an inward-facing portion of the second front side panel such that the fourth anti-skid element contacts the skin of a wearer of the absorbent article when the second fastening tab is in a fastened configuration.

42. The absorbent article of claim 23, wherein at least one of the first and second anti-skid elements is integrally formed with its respective fastening tab.

* * * * *